Feb. 23, 1954 R. ROMY Plant Pat. 1,258
RASPBERRY PLANT
Filed Dec. 23, 1952
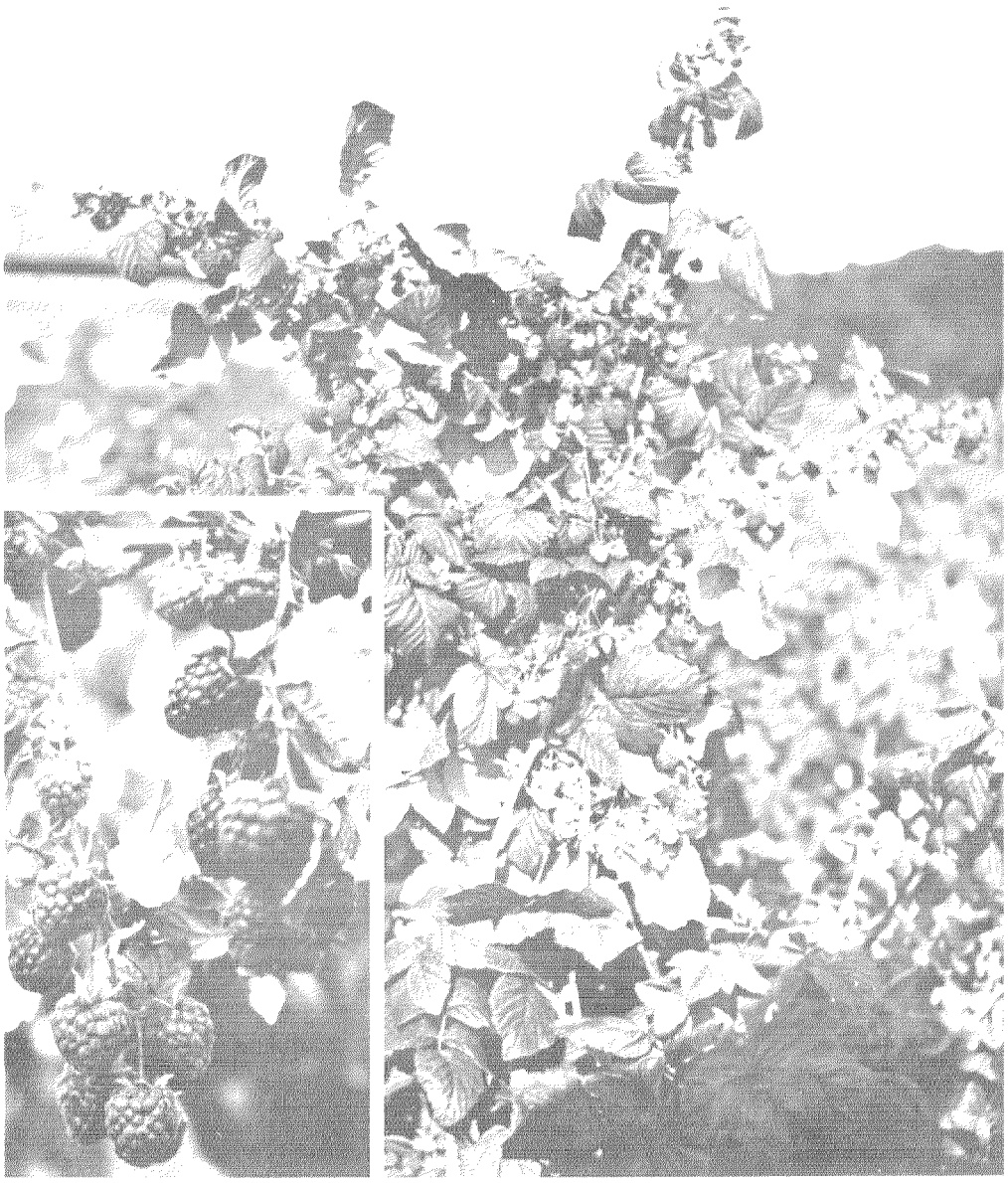
Inventor
Robert Romy
By: Robert Cobb
attorneys Patented Feb. 23, 1954 Plant Pat. 1,258

UNITED STATES PATENT OFFICE 1,258

RASPBERRY PLANT

Robert Romy, Geneva, Switzerland, assignor to W. Hauenstein Sohne, Rafz (Zurich), Switzerland, a firm of Switzerland Application December 23, 1952, Serial No. 327,707

1 Claim. (Cl. 47—62)

The present invention relates to a new and distinct variety of raspberry plant of the everbearing type and which was originated by me as a selected seedling derived from seeds obtained from the variety known as "Lloyd George" (unpatented).

For many years, I have been interested in growing and in experimenting with raspberry plants, and during the years, I have grown and tested most all of the known varieties, some of which I grew from seed, including, among others, the variety called "Lloyd George." In planting some seeds from the latter variety, I produced the present new variety which generally resembles the variety "Lloyd George" in respect to the shape and color of the foliage, the thorniness of the young shoots, and the shape and color of the berries or fruit, but which substantially differs from the parent variety, as well as from all other raspberry varieties of which I am aware, in respect to certain characteristics which are of great importance, particularly from a commercial standpoint.

Among the outstanding novel characteristics of my new variety of raspberry plant are its truly everbearing habit of growth, its continuous production of numerous shoots throughout the growing season and which mature and bear fruit the first season, its exceedingly heavy bearing habit averaging in berry production from 3 to 5 kilograms per plant, and its habit of relatively low bush growth averaging about 120 centimeters in height, thus making it unnecessary to tie up or otherwise support the plants.

In most of the cultivated varieties of raspberry plants which are known in commerce, as well as in the wild varieties, the buds appear on the new shoots in the course of the summer growing season, but do not develop until the following season. In the remontant varieties, the buds appear at the same time, but usually blossom in the fall, at least on some of the shoots. An important characteristic of the present new variety is that all of the shoots start blooming at once, no matter at what season or time they appear. This accordingly means that the buds do not pass through a period of repose before blossoming, as is customary in most of the known varieties. Since long shoots are formed on my new variety during the entire period of vegetation, the variety bears fruit practically without interruption from the beginning of the season until the first heavy frost.

Accordingly, my new variety cannot be likened to the usual remontant varieties, but rather to the contrary, it more properly must be considered as a mutant which I have achieved from deliberately planting seeds of the variety "Lloyd George," as performed in my cultivated gardens at Meyrin, a village near Geneva, Switzerland.

In addition to the aforementioned distinctions, my new variety is still further distinguished from the known raspberry varieties, including "Lloyd George" by its berries or fruit which are rather large in size, conical in shape, aromatic, and having a rather pronounced acidity. Although the production of the fruit is unusually heavy, the younger shoots tend to support the older ones which have already borne blossoms or are bearing fruit, and this characteristic, together with the relatively low-growing bush habit of growth of the plant, makes it unnecessary to use stakes, wires, or other supports for the plants, which is a very important and a distinct advantage when my new variety is employed for commercial production.

Asexual reproduction of my new variety by layering at Meyrin, a village near Geneva, Switzerland, shows that the foregoing characteristics and distinctions come true to form and are established and transmitted through succeeding propagations.

The accompanying drawing shows specimens of my new variety, with the fruit and foliage in different stages of development.

The following is a detailed description of my new variety, with color terminology in accordance with general color terms of ordinary dictionary significance:

Breeding: Seedling. Derived from mutation of seeds of the variety "Lloyd George."

Type: Everbearing; low-growing bush, averaging about 120 cm. in height. Dates first and last picking—about June 20th to late November, or until first heavy frost.

Plant: (Observations made from specimens grown at Meyrin, near Geneva, Switzerland.)

*Growth.*—Vigorous; numerous lateral shoots; leaves start developing as soon as stem rises from the ground, usually early in March.

*Root.*—Medium vigor; numerous buds on the roots.

*Crown.*—Branched; medium size.

*Canes and branches.*—Erect; stiff, do not bend. Young shoots—have pale green stem; slightly pubescent, but not glandulous; numerous thorns; stems not waxy.

*Thorns.*—More concentrated at the base of the primary canes; enlarged at base, suddenly narrowing at tips; straight; fairly strong, but cause little trouble when plants are pulled up. Size—short (2 to 3 mm.); slender. Color—dark reddish-brown throughout.

*Leaves.*—Many; medium size; about 14 to 15 cm. long, inclusive of petiole. Petiole—medium length (about 4 cm.); stout; very slightly thorny, with few reddish-brown thorns. Pubescence—wanting. Groove—shallow, but longer than that of the lateral. Blade of central leaflet—exceeds lateral. Serrations—irregular; broadly ovate; glabrate; apex tinged with green. Leaflet surface—upper side—dull; rugose. Color—dark green. Lower side—color—medium green. Pubescence—abundant.

*Runners.*—Appear during fruiting season; numerous; stocky.

*Flower stems.*—Long; inflorescence protected by foliage.

Bloom: Early; in bunches, with a rather robust stem; pedicel of each blossom is thin but robust (15 to 25 mm. in length), with a few brown thorns but no glands; sepals about 7 to 10 mm. long.

*Color.*—White petals.

*Date first bloom.*—About May 20th.

*Date full bloom.*—During entire summer growing season.

*Flowers.*—Many.

*Breadth.*—Primary—8 mm. Secondary—10 mm.

*Filaments of stamens.*—Short; perfect.

*Pollen.*—Medium abundance.

Fruiting stems: Long; slender; decumbent.

*Radical.*—Shorter than main truss.

*Branches of truss.*—Many.

Soil where grown: Sandy; loamy; well-drained.

Culture: Frequent; demands abundant nourishment due to fast-growing habit.

Frost resistance: Excellent resistance to frost; has withstood temperatures as low as 3°; crops have persisted until as late as November 19th.

Drought resistance: Medium.

Fruit:

*Condition when described.*—Prime.

*Date described.*—September 25th.

*Size.*—Uniform; medium large; constant throughout season; very easily separated from thalamus. Average fruit length—20 mm. Breadth—15 mm. Thickness—15 mm.

*Form.*—Uniform; regular; conical and obtuse, but rather broad at tip; apex rounded; fragrant; styles not very visible and fall easily.

*Stems.*—Radical—slender. Pubescence—scant; spreading.

*Calyx.*—Even with surface; free; medium size. Upper surface—color—light green. Pubescence—abundant. Lower surface—color—pale green. Pubescence—abundant. Segments—5 in number. Length—6 mm. Breadth—3 mm. Form—Lanceolate.

*Epicalyx.*—Wanting.

*Surface.*—Shiny and glossy but covered with very fine hairs, without wax. Color—dark red.

*Core.*—Hollow. Color—red.

*Flesh.*—Juicy. Color—red. Texture—soft; fine.

*Flavor.*—Subacid; aromatic.

*Quality.*—Good. Shipping quality—fair.

*Use.*—Market and dessert.

I claim:

A new and distinct variety of raspberry plant, substantially as herein shown and described, characterized particularly as to novelty by its everbearing habit, by its relatively erect and low-growing bush habit of growth, by its production of numerous shoots throughout the growing season, beginning with the first season, which mature and bear fruit the same season, and by its consistently heavy and regular fruit production.

ROBERT ROMY.

No references cited.